(12) United States Patent
Cronenberg

(10) Patent No.: US 9,468,721 B2
(45) Date of Patent: Oct. 18, 2016

(54) INJECTION DEVICE WITH AUTOMATED SUBSTANCE COMBINING FEATURE

(75) Inventor: Richard Cronenberg, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 45 days.

(21) Appl. No.: 14/118,184

(22) PCT Filed: May 19, 2011

(86) PCT No.: PCT/US2011/000897
§ 371 (c)(1),
(2), (4) Date: Nov. 15, 2013

(87) PCT Pub. No.: WO2012/158137
PCT Pub. Date: Nov. 22, 2012

(65) Prior Publication Data
US 2014/0094776 A1  Apr. 3, 2014

(51) Int. Cl.
*A61M 5/20* (2006.01)
*A61M 5/24* (2006.01)
*A61M 5/34* (2006.01)

(52) U.S. Cl.
CPC ......... *A61M 5/2066* (2013.01); *A61M 5/2033* (2013.01); *A61M 5/2448* (2013.01); *A61M 5/347* (2013.01); *Y10T 29/49826* (2015.01)

(58) Field of Classification Search
CPC ........... A61M 5/2448; A61M 5/2066; A61M 5/2033; A61M 5/3158; A61M 5/3243; A61M 2005/2073; A61M 5/20; A61M 5/31501; A61M 5/31596; A61M 5/3293; A61M 5/284; A61M 5/31571
See application file for complete search history.

(56) References Cited

U.S. PATENT DOCUMENTS

| | | | |
|---|---|---|---|
| 1,551,159 A * | 8/1925 | Kulik | A61M 5/32 604/241 |
| 4,214,584 A | 7/1980 | Smirnov et al. | |
| 4,822,340 A * | 4/1989 | Kamstra | A61M 5/2066 604/135 |
| 5,549,575 A | 8/1996 | Giambattista et al. | |
| 6,193,698 B1 * | 2/2001 | Kirchhofer | A61M 5/31551 604/207 |

(Continued)

FOREIGN PATENT DOCUMENTS

| | | |
|---|---|---|
| JP | 2002-541929 A | 12/2002 |
| JP | 2006-527037 A | 11/2006 |

(Continued)

*Primary Examiner* — Kevin C Sirmons
*Assistant Examiner* — William Carpenter
(74) *Attorney, Agent, or Firm* — Dickinson Wright PLLC

(57) ABSTRACT

An injection device for automatically combining two substances, including a body and a cartridge displaceably disposed within the body having a first chamber for containing a first substance, a second chamber for containing a second substance, a first stopper displaceably disposed within the cartridge separating the first and second chambers, a second stopper displaceably disposed within the cartridge defining an end of the second chamber. The device also includes a needle hub displaceably disposed within the body having threads thereon for connecting a pen needle to the injection device. The device additionally includes a plunger displaceably disposed within the body, a biasing member, a sleeve, biased by the biasing member and communicating the bias to the plunger, and an activation button radially displaceable with respect to the body to selectively release the sleeve to drive the plunger and automatically mix the first and second substances.

19 Claims, 13 Drawing Sheets

(56) References Cited

U.S. PATENT DOCUMENTS

| | | | |
|---|---|---|---|
| 6,203,530 B1* | 3/2001 | Stewart, Sr. | A61M 5/2033 604/207 |
| 6,793,646 B1* | 9/2004 | Giambattista | A61M 5/2066 604/208 |
| 8,376,998 B2 | 2/2013 | Daily et al. | |
| 8,556,862 B2 | 10/2013 | Cronenberg et al. | |
| 2001/0009990 A1* | 7/2001 | Hostettler | A61M 5/2066 604/209 |
| 2006/0276756 A1* | 12/2006 | Francavilla | A61M 5/3129 604/198 |
| 2007/0129686 A1* | 6/2007 | Daily | A61M 5/2033 604/192 |
| 2008/0108953 A1* | 5/2008 | Moser | A61M 5/31553 604/224 |
| 2010/0010454 A1* | 1/2010 | Marshall | A61M 5/2033 604/208 |
| 2011/0201999 A1* | 8/2011 | Cronenberg | A61M 5/2066 604/89 |
| 2011/0202013 A1* | 8/2011 | Jeter | A61M 5/002 604/228 |
| 2011/0213315 A1 | 9/2011 | Sweeney et al. | |
| 2011/0257604 A1 | 10/2011 | Banik | |

FOREIGN PATENT DOCUMENTS

| | | | | |
|---|---|---|---|---|
| JP | 2007-504866 A | 3/2007 | | |
| WO | WO-2008148518 A1 | 12/2008 | | |
| WO | WO-2009103251 A1 | 8/2009 | | |
| WO | 2010033806 A2 | 3/2010 | | |
| WO | 2010033882 A2 | 3/2010 | | |
| WO | WO-2010033782 A2 | 3/2010 | | |
| WO | WO 2010033782 A2 * | 3/2010 | | A61M 5/002 |
| WO | WO 2010033806 A2 * | 3/2010 | | A61M 5/2066 |
| WO | 2010056367 A1 | 5/2010 | | |

\* cited by examiner

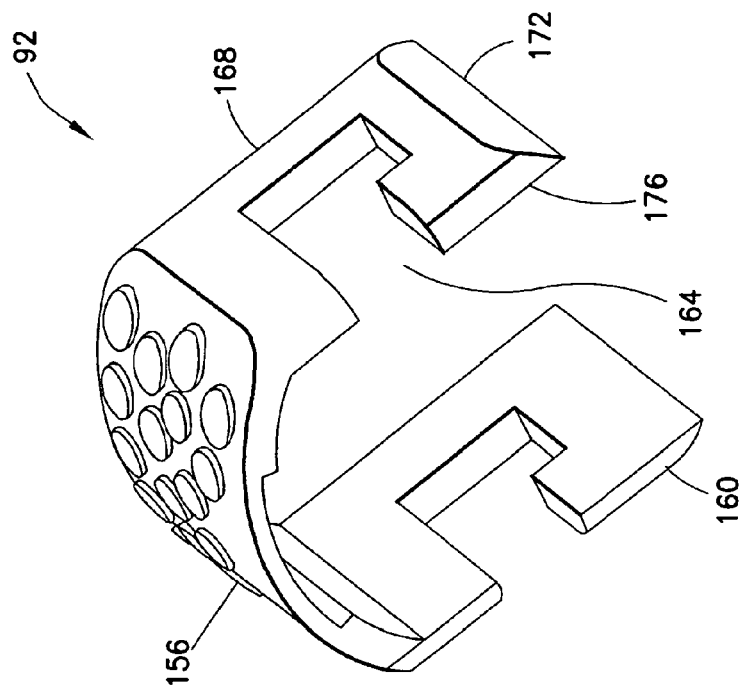
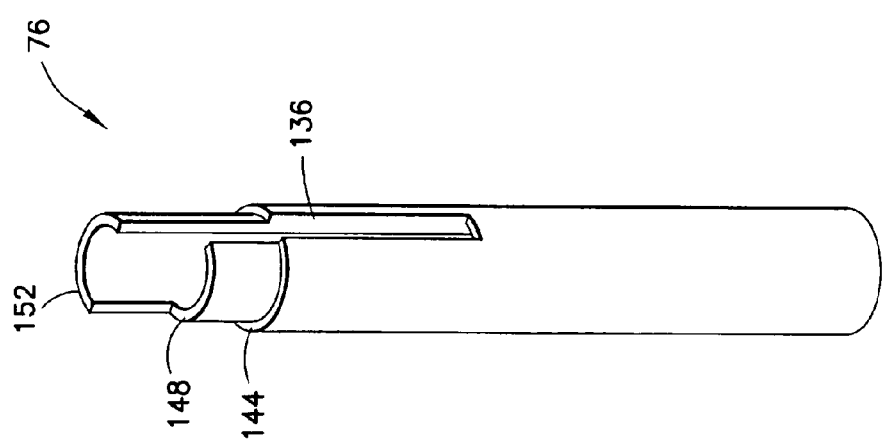

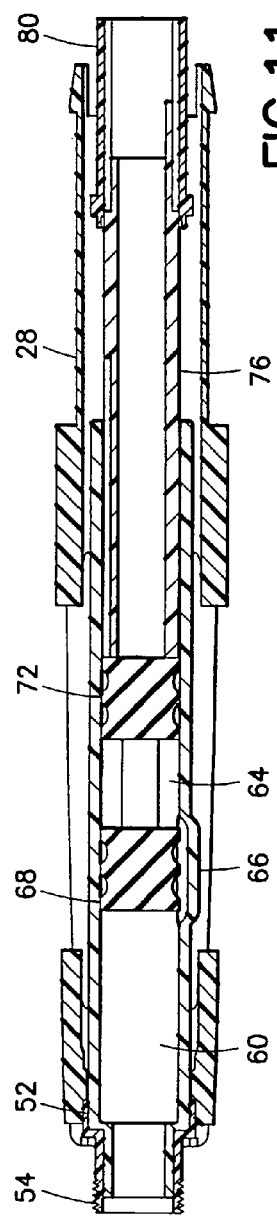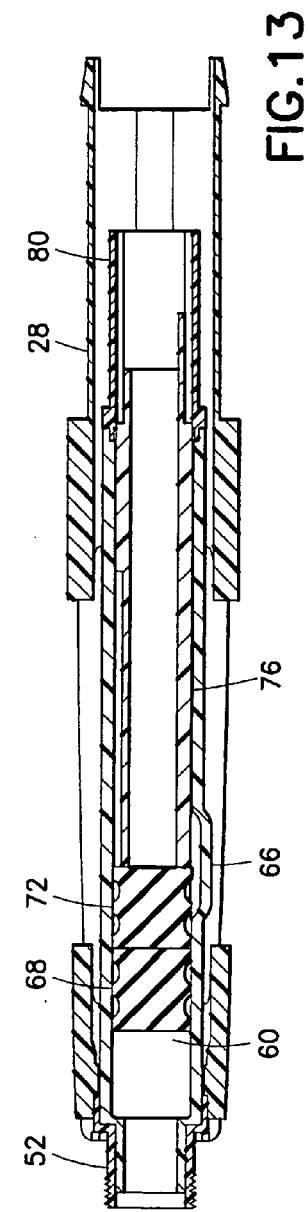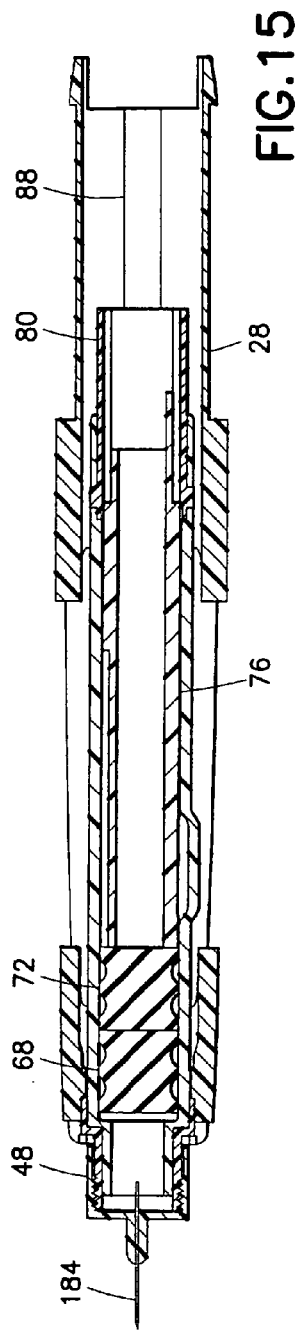

INJECTION DEVICE WITH AUTOMATED SUBSTANCE COMBINING FEATURE

CROSS-REFERENCE TO RELATED APPLICATIONS

This application is a National Stage Application under §371 of PCT Appl. No. PCT/US11/00897 filed 19 May 2011, the entirety of which is incorporated by reference herein.

FIELD OF THE INVENTION

The present invention relates generally to an injection device for dispensing a medicament, and more particularly to a pen-style injection device having an automated feature for combining at least two substances, such as reconstituting a lyophilized medicament prior to performing an injection.

BACKGROUND OF THE INVENTION

A wide variety of syringes and injection devices are commercially available. One type of injector that is popular is sometimes referred to as a pen-style injector because the injector body resembles a writing pen. Pen injectors have proven convenient in a wide variety of applications.

One difficulty associated with using conventional pen-style injectors occurs when the drug or medicament that is to be administered is provided in a lyophilized form. Lyophilized substances typically are supplied in a freeze-dried form that needs to be mixed with a liquid to reconstitute the substance into a form that is suitable for injection. Other substances that require reconstitution are provided in powder form. Under some circumstances, the reconstitution procedure must be performed carefully and at a controlled rate to ensure appropriate reconstitution.

One problem with conventional injectors is that they are dependent upon manual activation to complete a reconstitution procedure. The individual typically has to rotate different portions of the injector relative to each other using a screw-type action to move components within the injector to complete a reconstitution process. Examples of such devices are shown in U.S. Pat. No. 4,874,381 issued to Vetter, and U.S. Pat. No. 4,968,299 issued to Ahlstrand et al., both of which are incorporated by reference in their entirety into this specification. In other designs, relative axial movements are used to accomplish the reconstitution. Such procedures can prove difficult for some individuals and potentially introduce ergonomic concerns.

Moreover, manual reconstitution procedures typically cannot be performed at a consistently controlled rate. Certain lyophilized substances require reconstitution at a controlled rate to ensure that the lyophilized substance is appropriately reconstituted. For example, some medicaments will foam up if the reconstituting liquid is introduced too quickly. A foamed medicament is typically not suitable for injection and, therefore, manual reconstitution procedures present the possibility for requiring an extended waiting period before administering a particular dosage. Additionally, there may be uncertainty regarding whether the substance is ready for making an injection.

Another potential problem associated with manually activated pen-style injectors is that the reconstitution process may not be performed completely. Without appropriate controls, under some circumstances, it is possible for an individual to fail to completely reconstitute the lyophilized or powder-form medicament. Under such circumstances, the efficacy of the incompletely reconstituted medicament may be reduced or eliminated.

SUMMARY OF THE INVENTION

An aspect of the present invention is to provide an automated combining or reconstitution feature that is not dependent upon manual operation and consistently provides a controlled combination or reconstitution rate.

The foregoing and/or other aspects of the present invention are achieved by providing an injection device for automatically combining two substances, the device including a body and a cartridge displaceably disposed within the body. The cartridge has a first chamber for containing a first substance, a second chamber for containing a second substance, a first stopper displaceably disposed within the cartridge and separating the first and second chambers, and a second stopper displaceably disposed within the cartridge and defining an end of the second chamber. The device also includes a needle hub displaceably disposed within the body. The needle hub has threads thereon for connecting a pen needle to the injection device. The device additionally includes a plunger displaceably disposed within the body, a biasing member, a sleeve, biased by the biasing member and communicating the bias to the plunger, and an activation button radially displaceable with respect to the body to selectively release the sleeve to drive the plunger and automatically mix the first and second substances.

The foregoing and/or other aspects of the present invention are also achieved by providing an injection device for automatically combining two substances, the device including a body and a cartridge displaceably disposed within the body. The cartridge has a first chamber for containing a first substance, a second chamber for containing a second substance, a first stopper displaceably disposed within the cartridge and separating the first and second chambers, and a second stopper displaceably disposed within the cartridge and defining an end of the second chamber. The device also includes a needle hub displaceably disposed within the body and having threads thereon. The device additionally includes a plunger displaceably disposed within the body, a biasing member, a sleeve, biased by the biasing member and communicating the bias to the plunger, and an activation button displaceable with respect to the body to selectively release the sleeve to drive the plunger and displace the needle hub to expose the threads for connection with a pen needle, and automatically mix the first and second substances.

The foregoing and/or other aspects of the present invention are also achieved by providing a method of manufacturing an injection device, including the operations of inserting a cartridge into a body, inserting a plunger into the body to substantially axially align the plunger and the cartridge, and inserting a sleeve onto an end of the plunger. The method also includes the operations of assembling a radially displaceable activation button with the body to selectively restrain the sleeve from distal displacement, and assembling a biasing member in the injection device to bias the sleeve.

The foregoing and/or other aspects of the present invention are also achieved by providing a method of operating an injection device having a cartridge displaceably disposed within a body and having a first chamber for containing a first substance, a second chamber for containing a second substance. The method includes the operations of radially displacing an activation button to release a biased sleeve, to expose the threads of a needle hub and mix the first and second substances; rotating a knob to set a dosage; and displacing the knob to expel the dose from the injection device.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which:

FIGS. 5 and 6 are perspective views of a plunger of the device of FIG. 1;

FIG. 7 is a perspective view of an activation button of the device of FIG. 1;

FIG. 11 is a partial cross-sectional view of the device of FIG. 1 illustrating an intermediate stage of an automatic reconstitution process;

FIG. 13 is a partial cross-sectional view of the device of FIG. 1 illustrating the end of the reconstitution process and the activated state;

FIG. 15 is a partial cross-sectional view of the device of FIG. 1 illustrating the end of the injection process;

DETAILED DESCRIPTION OF EXEMPLARY EMBODIMENTS

Figure 1:
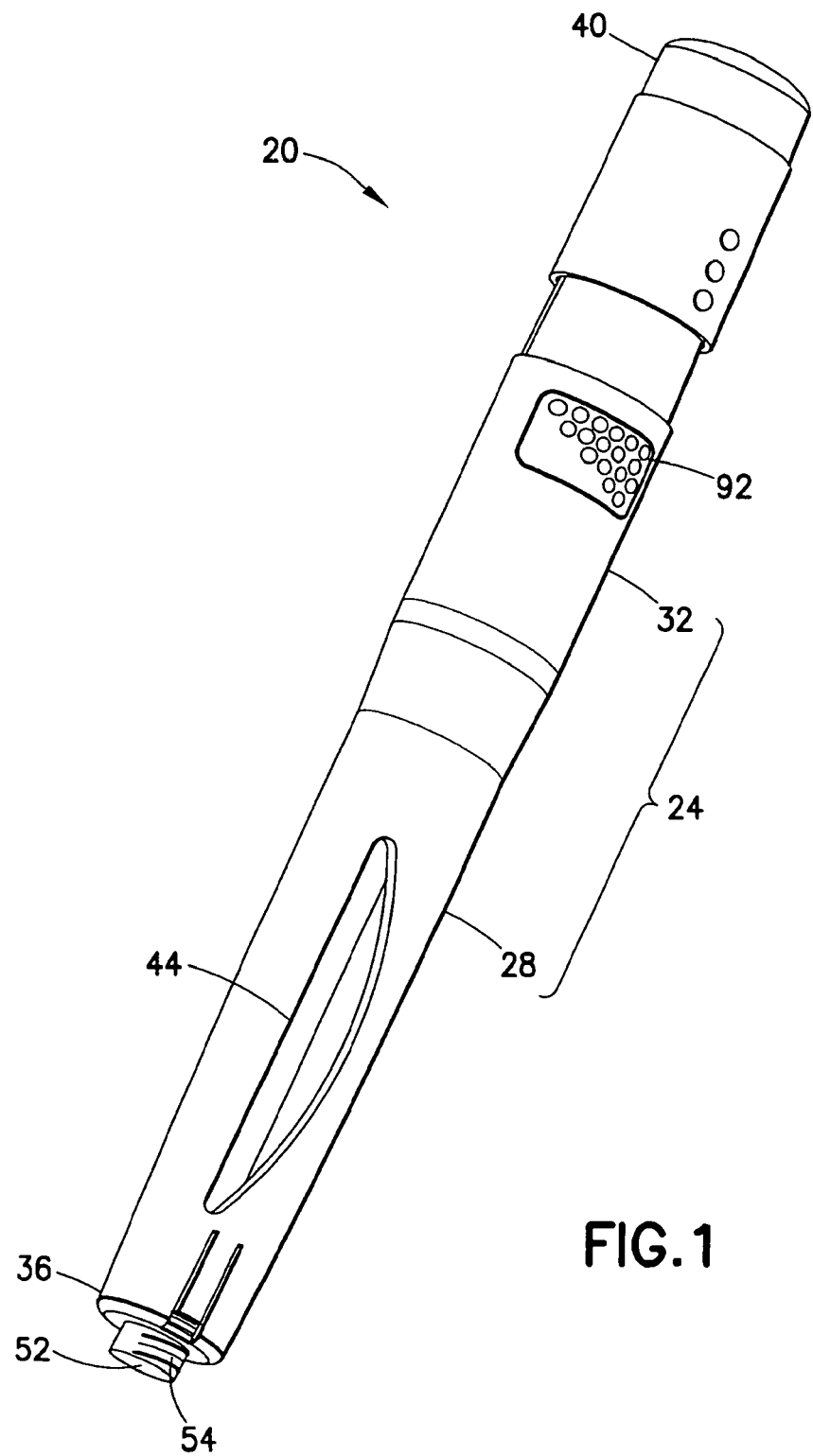
FIG. 1 is a perspective view of an injection device in accordance with an embodiment of the present invention.

Reference will now be made in detail to embodiments of the present invention, examples of which are illustrated in the accompanying drawings, wherein like reference numerals refer to the like elements throughout. The descriptions of these embodiments exemplify the present invention by referring to the drawings.

Figure 2:
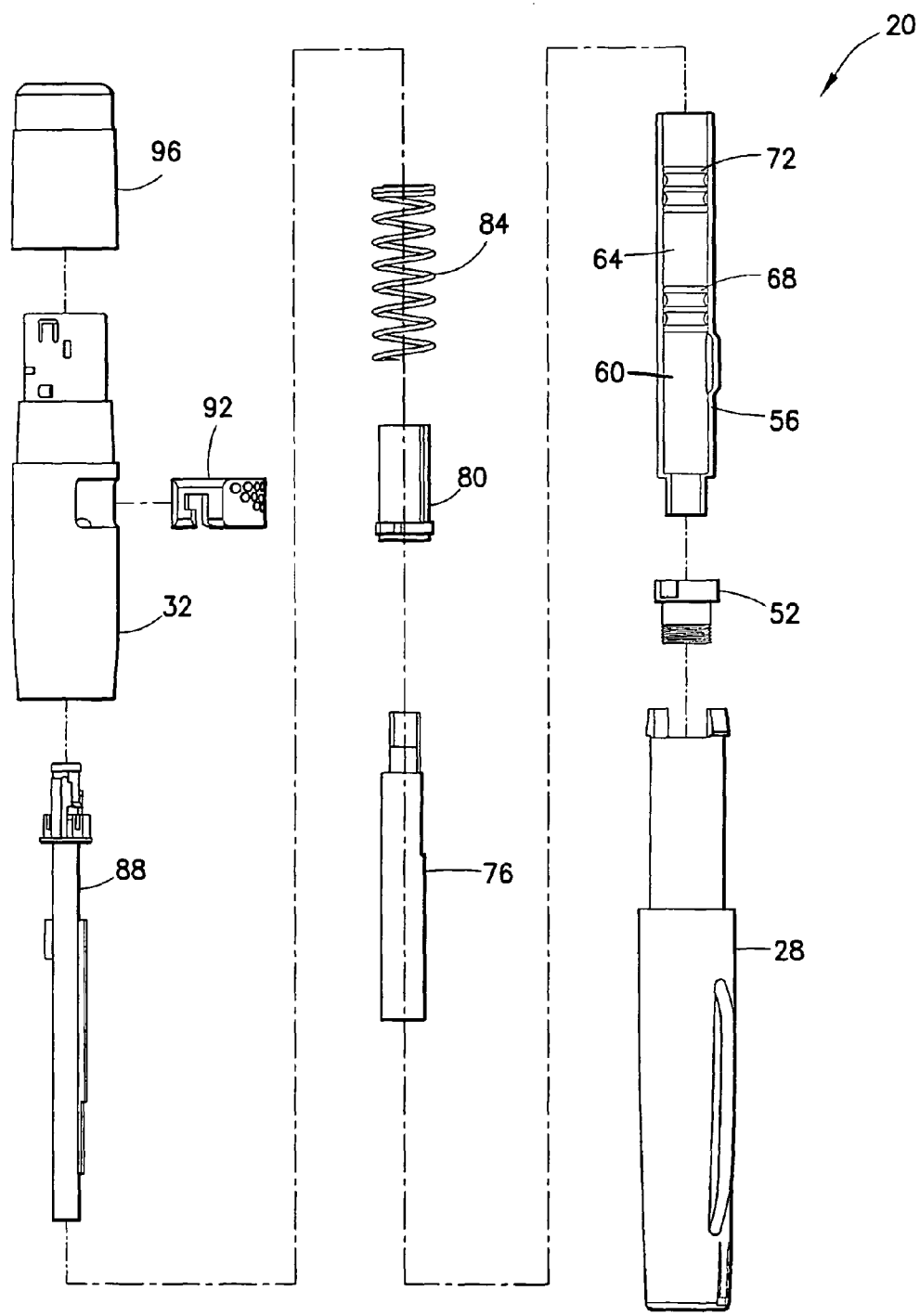
FIG. 2 is a perspective exploded view of the device of FIG. 1.

FIGS. 1 and 2 diagrammatically illustrate a pen-style injection device or injector 20 for automatically combining two substances. The injector 20 has a body 24 that is adapted to fit within an individual's hand and includes a lower body 28 and an upper body 32. The injector 20 includes a distal, front, or forward end 36 and a proximal, back, or rear end 40. A viewing window 44 allows an individual to see the contents of the injector before or after an injection. The illustrated example is a device for delivering a single dosage and is intended to be a single-use device. Additionally, in the illustrated example, the injector 20 is used to perform a hypodermic injection using a pen needle 48, as described in greater detail below. This invention is not limited, however, to such hypodermic injectors.

This specification refers to "distal," "forward" or "front" interchangeably and "proximal," "rear" or "back" interchangeably to refer to directions or ends of various components. Those terms are used for illustration and discussion purposes only. The particular arrangement of components and their directions of movement contained in the illustrated examples are not to be construed in a limiting sense.

As shown in FIGS. 1 and 2, the injector 20 also includes a needle hub 52 displaceably disposed within the lower body 28 and a medicament container 56 displaceably disposed within the lower body 28. The needle hub 52 has threads 54 and is disposed at a distal end of the medicament container 56. According to one embodiment, the medicament container 56 is a prefilled cartridge 56. The cartridge 56 includes a first chamber 60 for containing a first substance and a second chamber 64 for containing a second substance. Preferably, the first and chamber 60 contains a lyophilized medicament and the second chamber 64 contains a liquid for reconstituting a lyophilized medicament. The first and second chambers 60 and 64 and selectively communicate through a communication passage (or communication channel or bypass) 66 so that the two substances can be combined as needed. The bypass 66 is axially longer than an axial length of a single stopper, as discussed in greater detail below. For purposes of illustration, the following discussion will describe reconstitution of a lyophilized medicament. Other mixing or combining operations are also possible.

The cartridge 56 also includes a first stopper 68 and a second stopper 72. The first stopper 68 is displaceably disposed within the cartridge 56 and separates the first and second chambers 60 and 64. The second stopper 72 is displaceably disposed within the cartridge 56 and defines a proximal end of the second chamber 64.

As described in greater detail below, the injector 20 further includes a plunger 76 that is displaceably disposed within the body 24 proximally with respect to the second stopper 72, and a sleeve 80 that is displaceably disposed within the body 24 to contact the plunger 76. Additionally, the injector 20 includes a biasing member 84 distally biasing the sleeve 80, a dosing stem 88 for setting a dosage, an activation button 92 radially displaceable with respect to the body 24, and a knob 96 fixedly connected to the dosing stem 88. As described in greater detail below, the activation button 92 is radially displaceable from a pre-activated position to a depressed position. In the currently preferred embodiment, the biasing member 84 is a spring 84. Other biasing members, such as gas springs, pressurized gas, electrically powered devices, or a combination of these may be suitable under certain circumstances.

Figure 3:
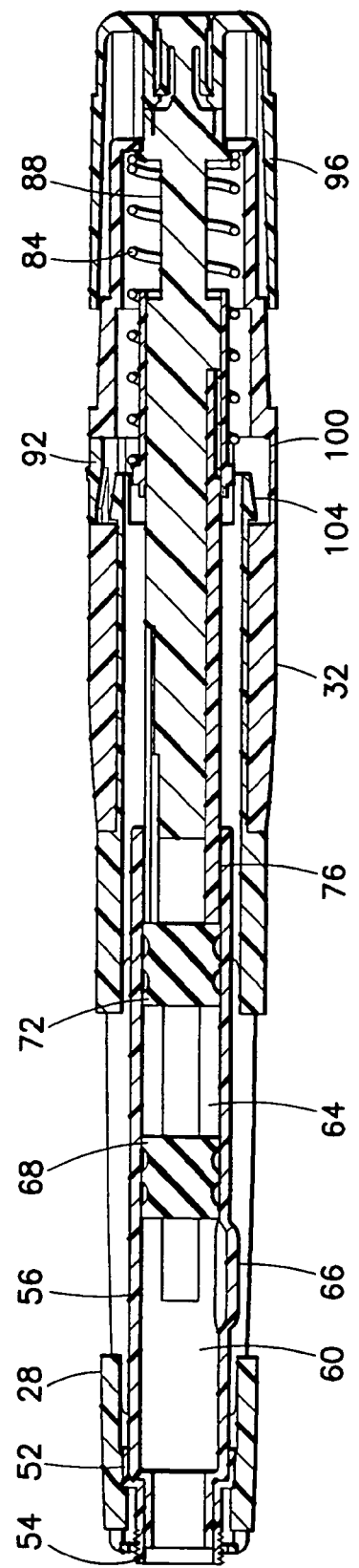
FIG. 3 is a cross-sectional view of the device of FIG. 1 illustrating a pre-activated state.

FIG. 3 is a cross-sectional view illustrating a pre-activated state of the injector 20. As shown in FIG. 3, the upper body 32 includes a radial recess 100 and the lower body 28 has a corresponding snap hook 104 for securing the lower body 28 with the upper body 32. FIG. 3 also shows the activation button 92 in the pre-activated position, in which the activation button 92 retains the sleeve 80 against the distal bias of the biasing member 84. Additionally, FIG. 3 shows that in the pre-activated state, the plunger 76 contacts both the sleeve 80 and the second stopper 72. Further, because of the positioning of the first stopper 68, in the pre-activated state, the bypass 66 is disposed entirely within the first chamber 60.

Figure 4:
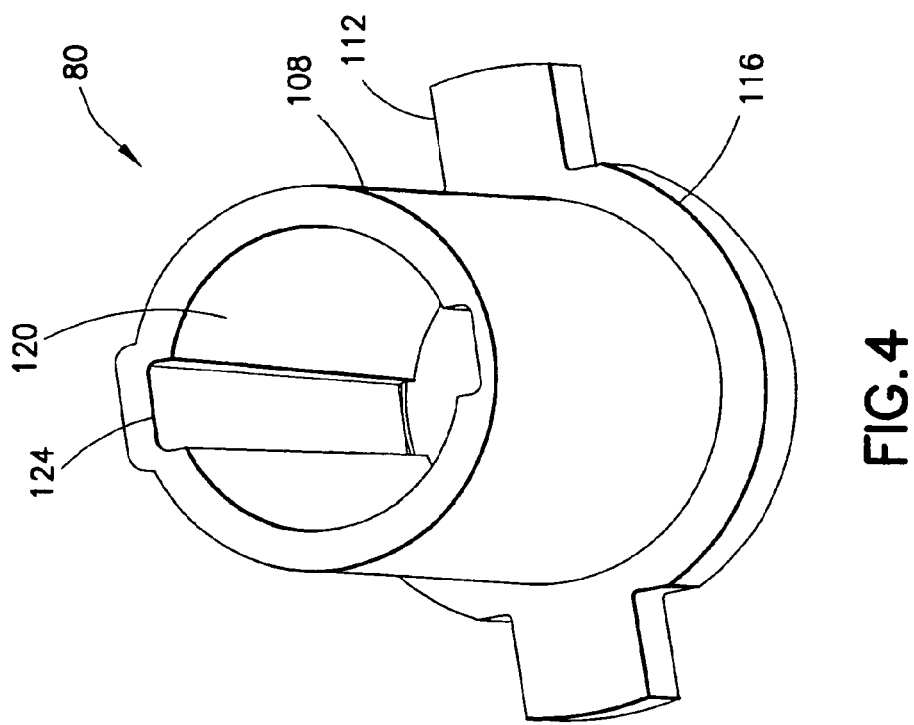
FIG. 4 is a perspective view of a sleeve of the device of FIG. 1.

FIG. 4 is a perspective view of the sleeve 80 of the injection device 20. The sleeve 80 includes a central portion 108 with the radial arm 112 extending radially from the central portion 108. The sleeve 80 also includes a circumferential flange 116 for receiving a distal end of the biasing member 84. According to one embodiment, the radial arm 112 extends from the flange 116 and the proximal surface of the flange 116 is substantially planar with the proximal surface of the radial arm 112. As described in greater detail below, an interior of the central portion 108 is an axial passage 120 that includes a pair of axial grooves 124 for slidably receiving the dosing stem 88. According to one embodiment, both the upper and lower bodies 28 and 32 have a pair of axial grooves for guiding the radial arms 112 of the sleeve 80 and substantially preventing rotation thereof.

Figure 5:
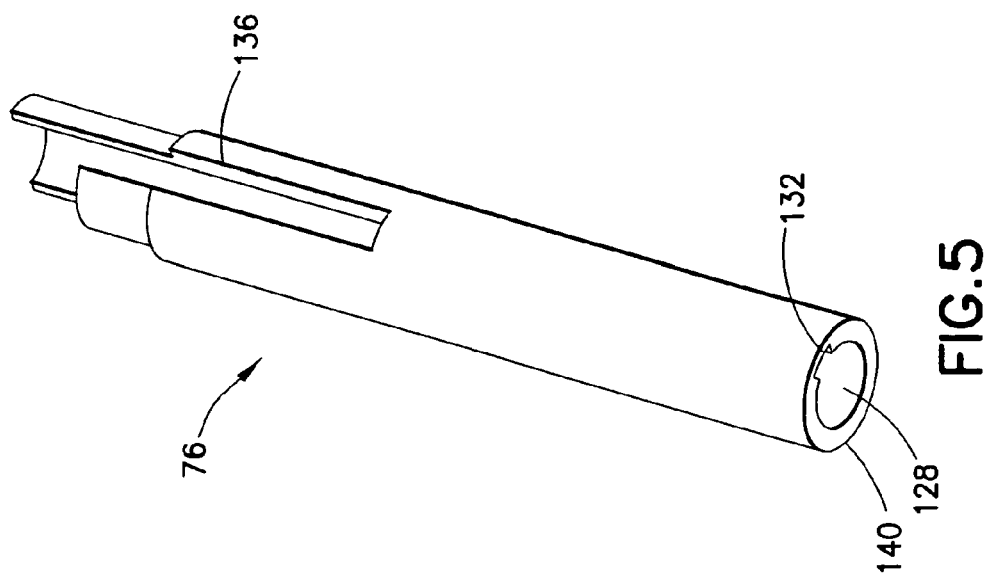

FIGS. 5 and 6 are perspective views of the plunger 76 of the injection device 20. An interior portion of the plunger 76 is an axial passage 128 that includes an axial groove 132 for slidably receiving the dosing stem 88, as discussed in greater detail below. The plunger 76 also includes an axial groove 136 for slidably receiving the dosing stem 88 and selectively preventing rotation thereof. A distal bearing surface 140 is disposed at a distal end of the plunger 76 for contacting the second stopper 72. Additionally, as shown in FIG. 6, and the plunger 76 includes a first circumferential flange 144 for receiving the sleeve 80, and second and third flanges 148 and 152 that, as described in greater detail below, act as a bearing surface for the dosing stem 88 during injection.

FIG. 7 is a perspective view of the activation button 92 of the injection device 20. The activation button 92 includes a user interface surface 156 and a pair of J-shaped, cantilevered arms 160 extending from the user interface surface 156. The cantilevered arms 160 each have a distal opening 164. Each of the cantilevered arms 160 has a first portion 168 extending from the user interface surface 156, an axial portion 172, and a return portion 176. The activation button 92 is radially displaceable relative to the body 24 from a pre-activated position to a depressed position.

Figure 8:
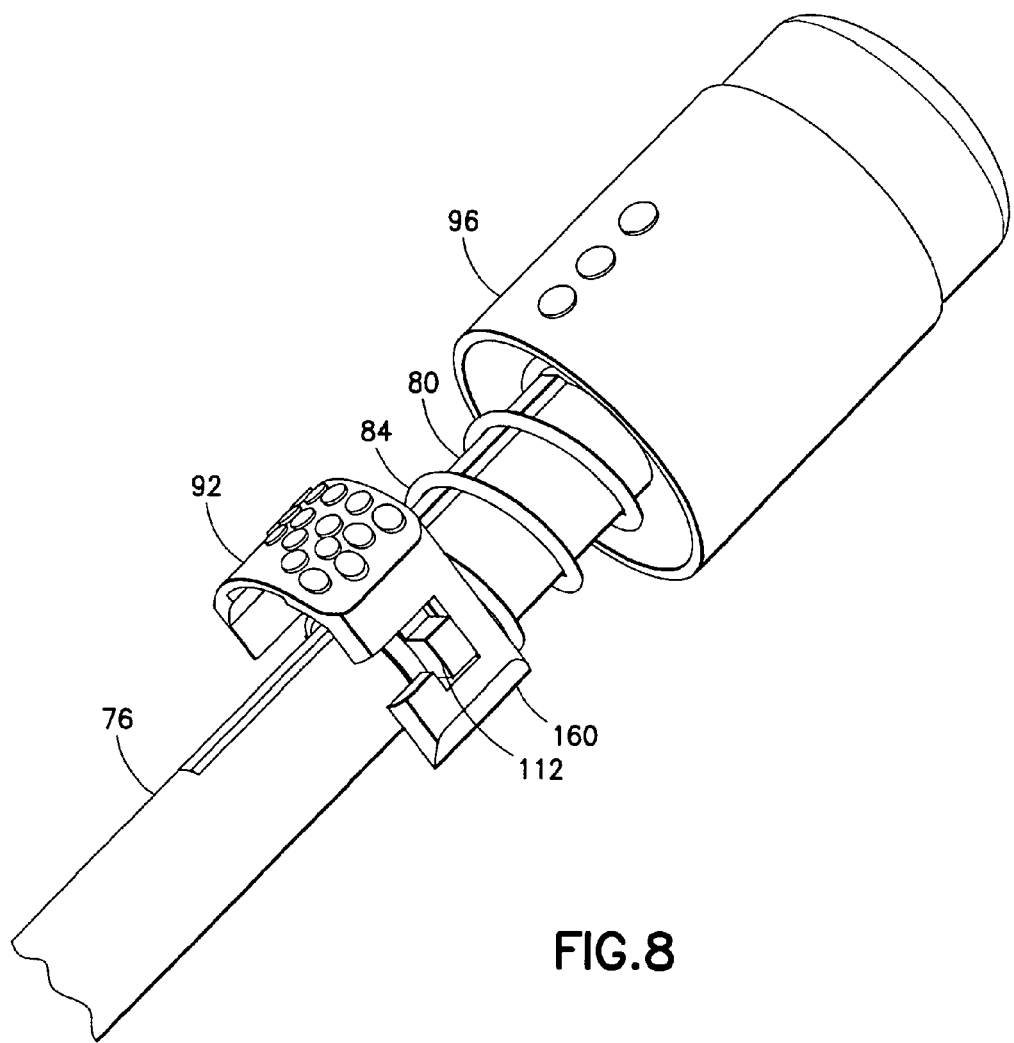
FIG. 8 is a perspective view of selected components of the device of FIG. 1 in the pre-activated state.
Figure 9:
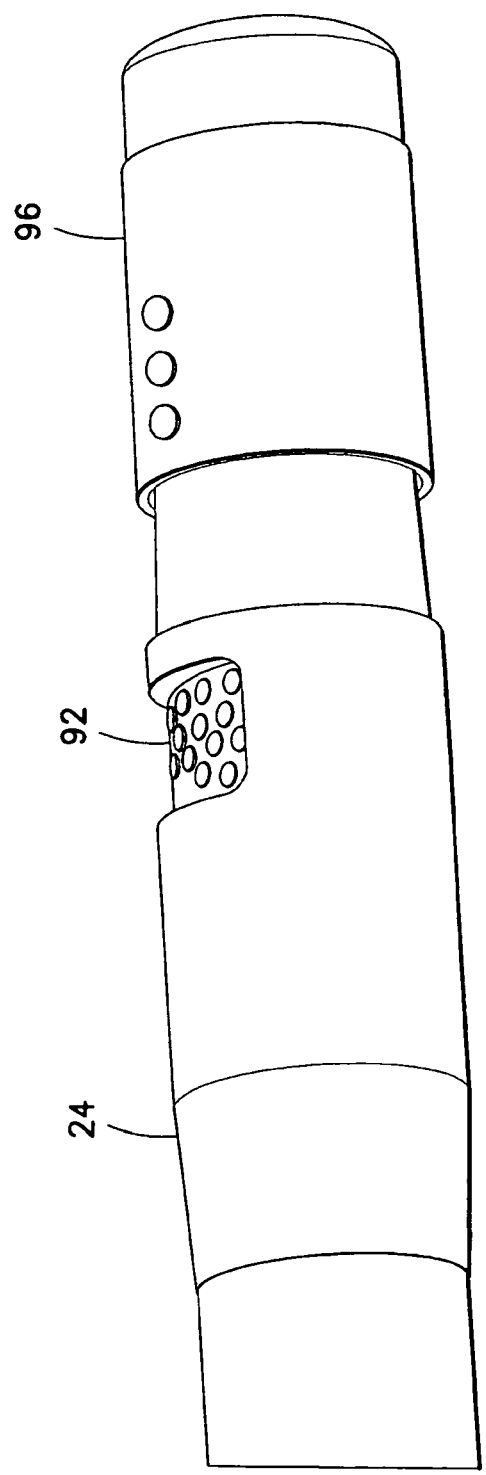
FIG. 9 is a partial perspective view of the device of FIG. 1 illustrating the activation button in a depressed position.
Figure 10:
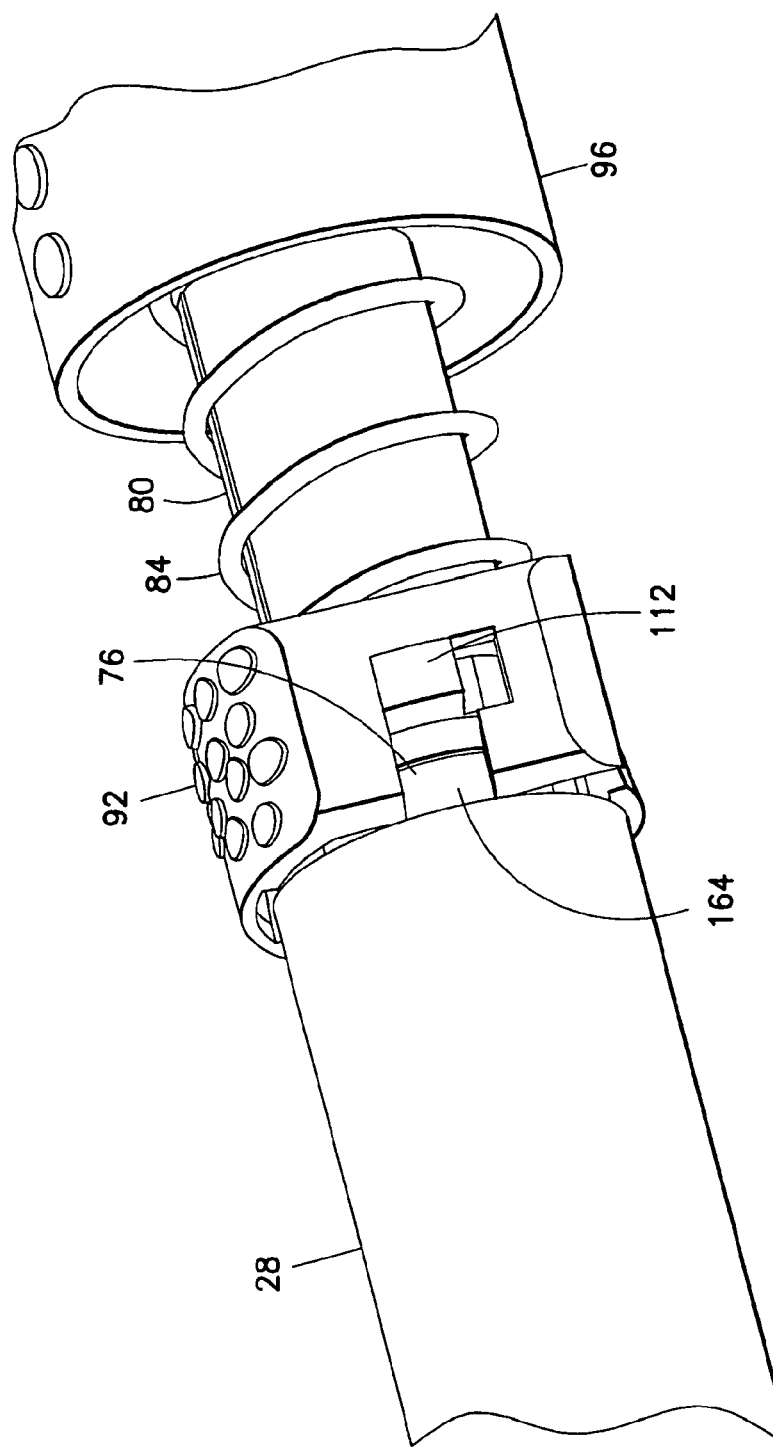
FIG. 10 is a perspective view of selected components of the device of FIG. 1 subsequent to depression of the activation button.

FIG. 8 is a perspective view of selected components of the injection device 20 in the pre-activated state. The remaining components are removed for clarity. As shown in FIG. 8, the activation button 92 is in the pre-activated position. In this position, the cantilevered arms 160 of the activation button 92 retain the radial arms 112 of the sleeve 80 against the distal bias of the biasing member 84. As shown in FIGS. 9 and 10, once the user depresses the activation button 92 and radially displaces the activation button 92 from the pre-activated position to the depressed position, the distal openings 164 of the cantilevered arms 160 align with the radial arms 112 of the sleeve 80. Subsequent to the displacement of the activation button 92 to the depressed position, the force from the biasing member 84 simultaneously distally displaces the sleeve 80 and the plunger 76, which contacts the sleeve 80.

This distal displacement of the plunger 76 also distally displaces the second stopper 72 and the needle hub 52. FIG. 11 illustrates an intermediate stage of the automatic reconstitution process. According to one embodiment, at least in part due to the friction between the second stopper 72 and the cartridge 56, the distal displacement of the plunger 76 distally displaces the needle hub 52 relative to the body 24 to expose the threads of the needle hub 52 for connection with the pen needle 48 prior to the mixing of the first and second substances.

Figure 12:
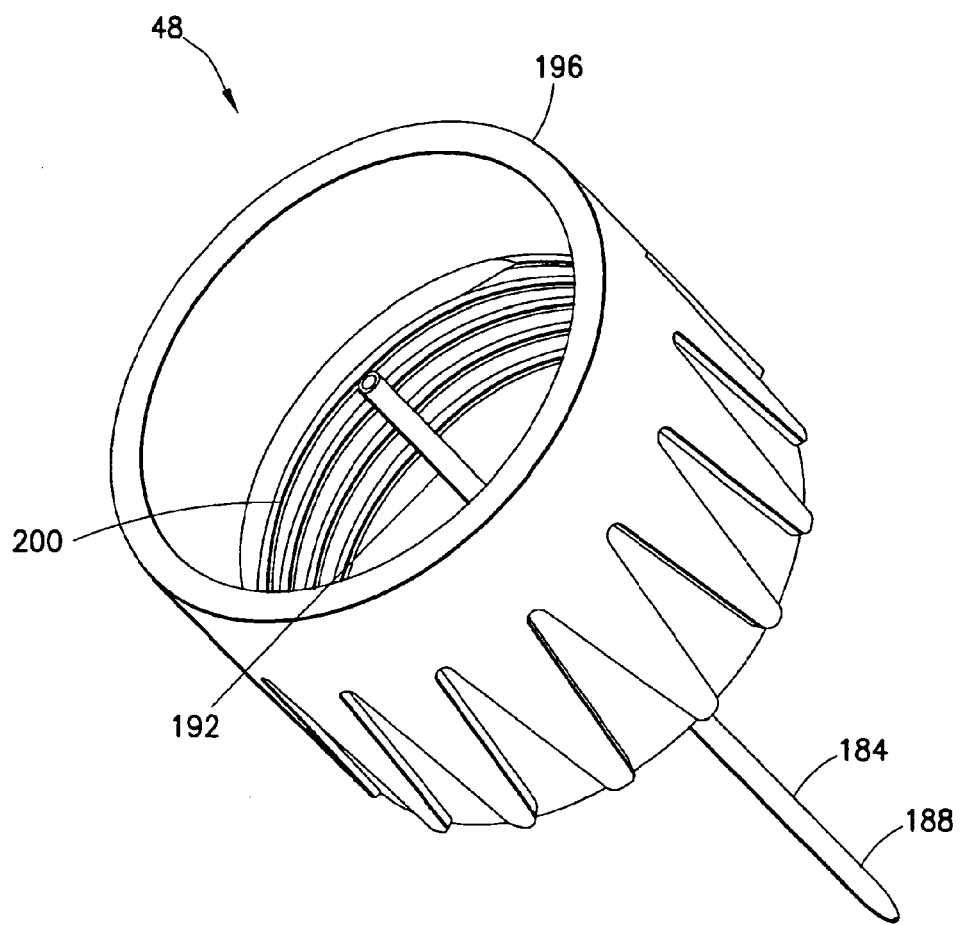
FIG. 12 is a perspective view of a pen needle for connecting to the device of FIG. 1.

FIG. 12 is a perspective view of an exemplary pen needle 48 for selective connection with the injection device 20. As shown in FIG. 12, the pen needle 48 includes a needle 184 having an external portion 188 for piercing the skin of the patient and an internal portion 192 for communication with the contents of the cartridge 56. The internal and external portions 188 and 192 are in fluid communication with each other. The pen needle 48 also includes a hub 196 for holding the needle 184. The hub 196 also has threads 200 corresponding to the threads 54 of the needle hub 52. According to the illustrated embodiment (for example, FIGS. 1 and 3) a portion of the threads 54 are exposed when the injection device 20 is in the pre-activated state. Because the threads 200 are distally spaced relative to the proximal end of the hub 196, however, the pen needle 48 cannot be connected with the threads 54 when the injection device 20 is in the pre-activated state. As discussed in greater detail below, this prevents a user from prematurely connecting the pen needle 48, and thereby helps to ensure proper mixing of the first and second substances. According to another embodiment that prevents premature connection of the pen needle 48, the threads 54 are disposed entirely within the lower body 28 when the injection device 20 is in the pre-activated state.

Referring back to FIG. 11, the fluid within the second chamber 64 also provides hydraulic pressure to distally displace the first stopper 68. At the intermediate stage illustrated in FIG. 11, the first stopper 68 is distally displaced to a position adjacent to the bypass 66. Because the bypass 66 is axially longer than an axial length of a single stopper, the first and second chambers 60 and 64 communicate via bypass 66. As the force of the biasing member 84 continues to act on the second stopper 72 via the sleeve 80 and the plunger 76, the second stopper 72 forces the fluid from the second chamber 64 into the first chamber 60, mixing the contents and reconstituting the lyophilized medicament.

Under the continuing force of the spring 84, the second stopper 72 forces substantially all of fluid into the first chamber 60 and then contacts the first stopper 68. Subsequently, the force of the spring 84 displaces the first and second stoppers 68 and 72 together until the first stopper 68 is disposed distally relative to the bypass 66, thereby sealing the first chamber with respect to the bypass 66. In this state, as shown in FIG. 13, the lyophilized medicament is reconstituted, and the injection device 20 is activated. According to one embodiment, at this stage, the fluid pressure in the first chamber 60 prevents further distal movement of the stoppers 68 and 72, and thus prevents further expansion of the spring 84.

Once activated, the user connects the pen needle 48 with the injection device 20. This process establishes a fluid connection with the needle 184 and the first chamber 60, and vents air from the first chamber 60, allowing the spring 84 to expand further and contact a mechanical stop. This final expansion of the spring 84 slightly displaces the first and second stoppers 68 and 72 and ejects a small amount of the reconstituted medicament from the needle 184, thereby priming the injection device 20.

Figure 14:
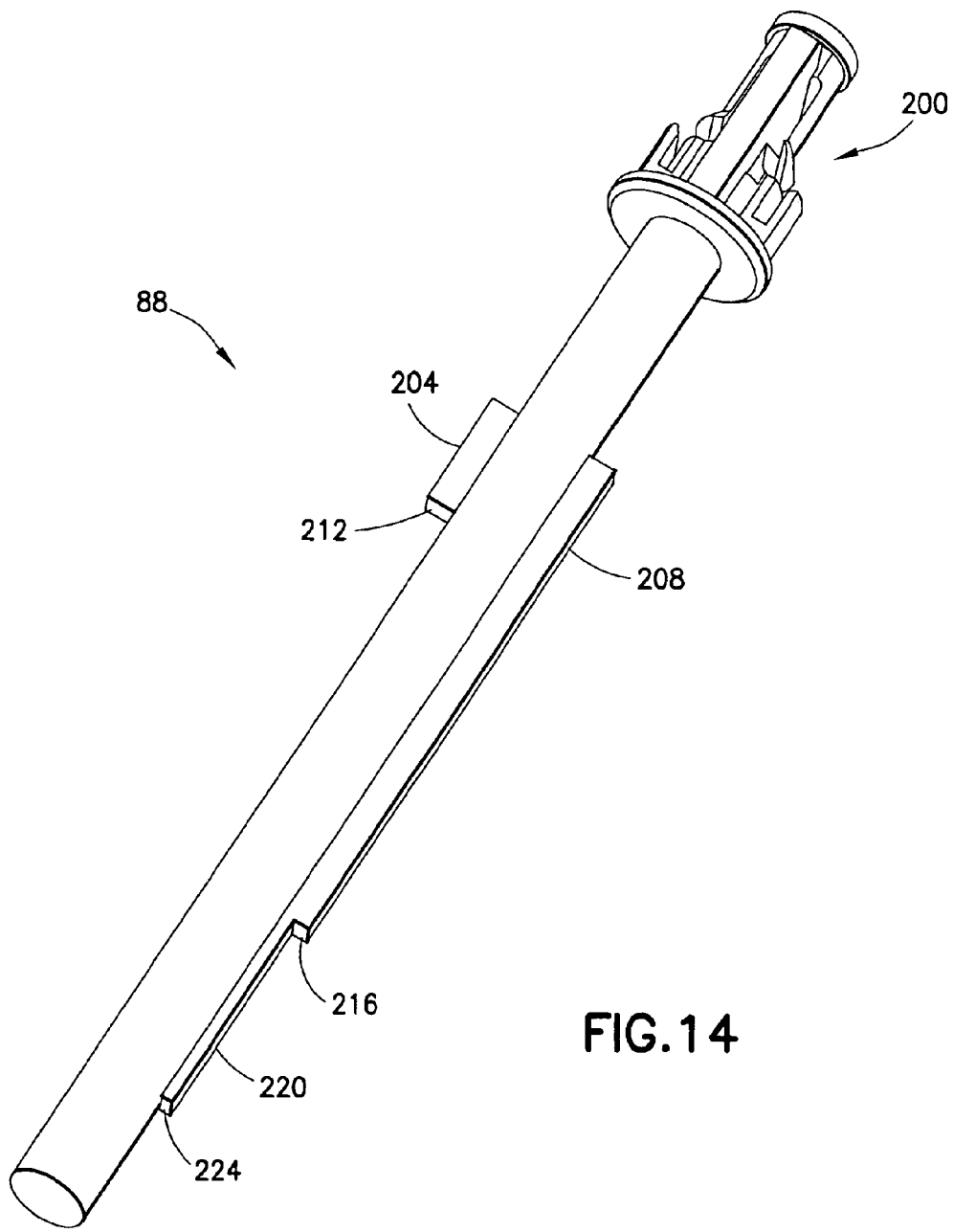
FIG. 14 is a perspective view of a dosing stem of the device of FIG. 1.

FIG. 14 is a perspective view of the dosing stem 88 of the injection device 20. The dosing stem 88 includes a knob-connecting mechanism 200 that interacts with a stem-connecting mechanism 202 (shown in FIG. 17) in the knob 96 to fixedly connect the dosing stem 88 and the knob 96. The dosing stem 88 also includes first and second keys 204 and 208 radially protruding from the dosing stem 88. Each of the first and second keys 204 and 208 has a distal bearing surface 212 and 216. In the pre-activated state, the first and second keys 204 and 208 are disposed within the axial grooves 124 of the sleeve 80. Additionally, a portion of the second key 208 is disposed within the axial slot 136 of the plunger 76, and a lower portion 220 of the second key 208 is disposed within the plunger axial groove 132 of the plunger 76. Thus, in the pre-activated state, the dosing stem 88 is prevented from rotating. Further, in the pre-activated state, the bearing surface 212 bears against the third flange 152 of the plunger 76 and the bearing surface 216 bears against the distal end of the axial slot 136 of the plunger 76.

Once the device is activated, the sleeve 80 and the plunger 76 have been sufficiently distally displaced that the first and second keys 204 and 208 no longer engage the sleeve 80 and the plunger 76. Accordingly, in this state, the user is able to distally displace and rotate the knob 96 (and thus, the dosing stem 88) to engage a dosage step 224 of the dosing stem 88 with the second flange 148 of the plunger 76 to set the dosage. Subsequent manual distal movement of the knob 96 will cause simultaneous distal movement of the plunger 76. As shown in FIG. 15, this displacement of the plunger 76 distally displaces the first and second stoppers 68 and 72 to cause the reconstituted medicament to be expelled from the tip of the needle 184 to complete a hypodermic injection.

Figure 16:
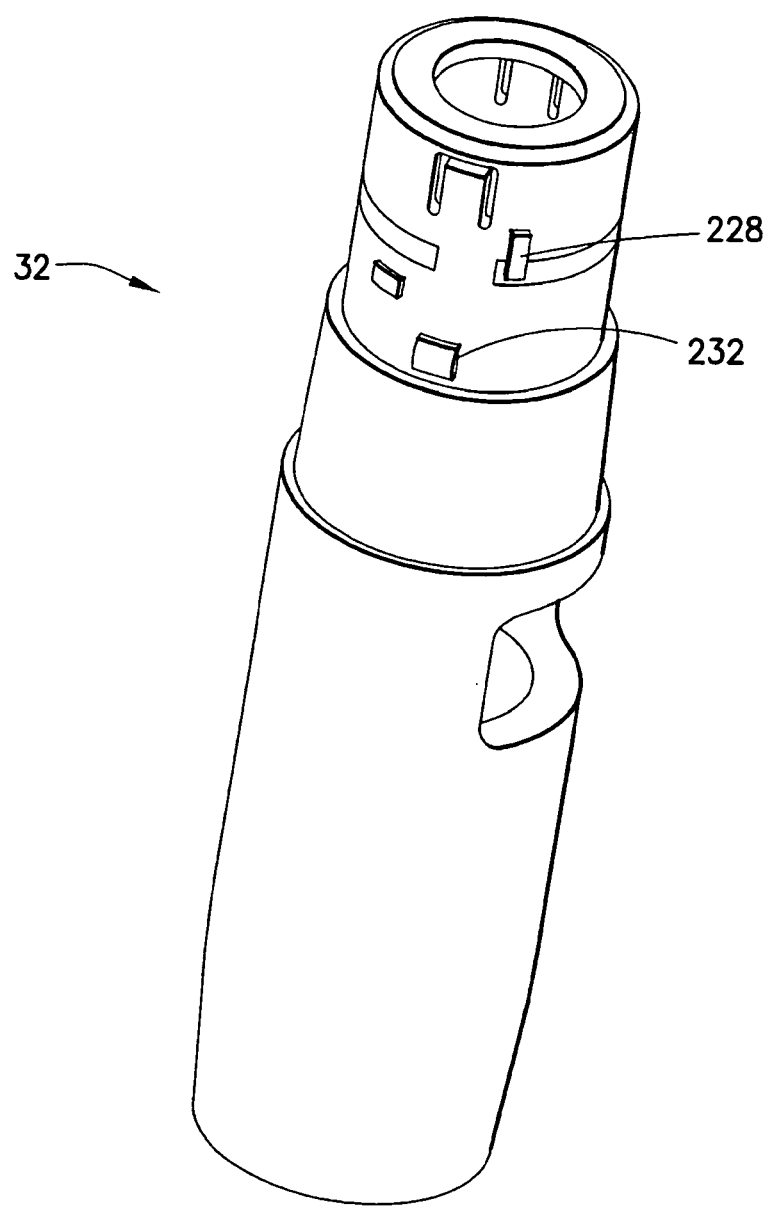
FIG. 16 is a perspective view of an upper body of the device of FIG. 1.
Figure 17:
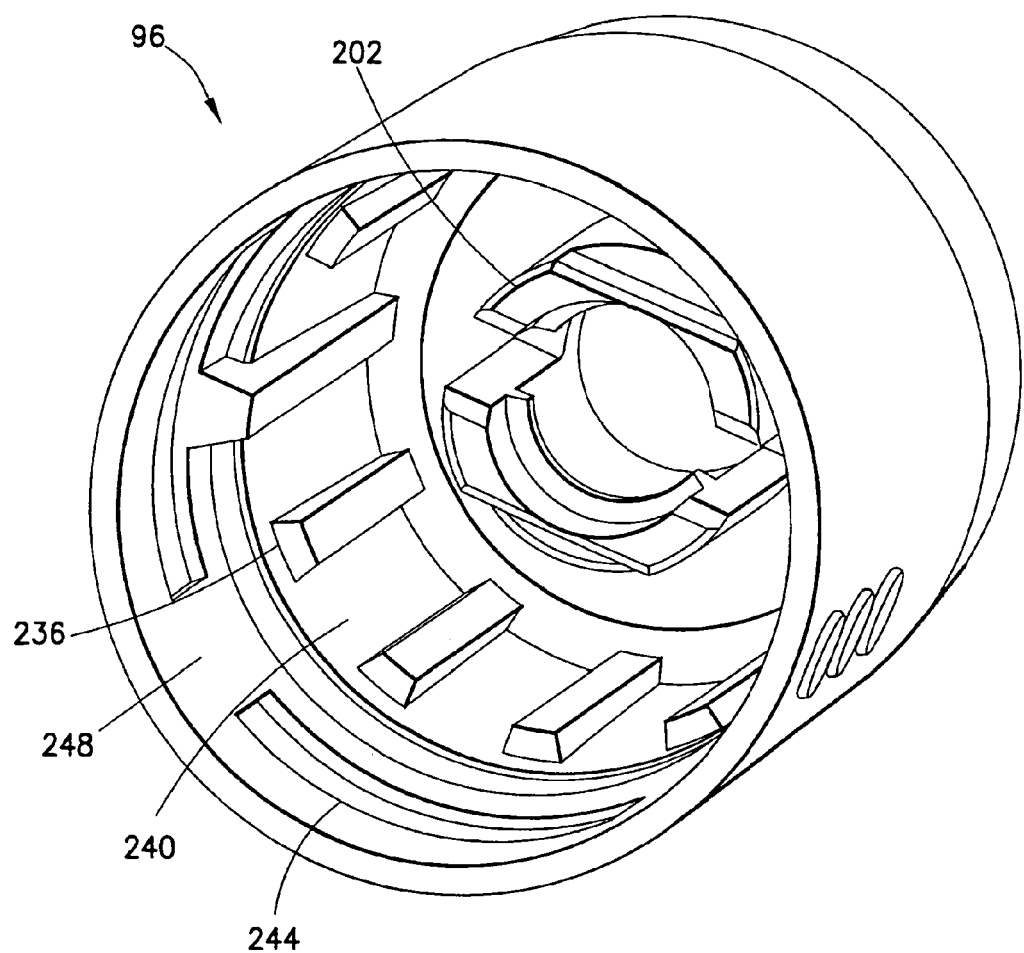
FIG. 17 is a perspective view of a knob of the device of FIG. 1.

FIG. 16 is a perspective view of the upper body 32. The upper body 32 includes a pair of dosage keys 228 and a pair of locking protrusions 232, all of which radially protrude from the upper body 32. As shown in FIG. 17, to facilitate dosage delivery, knob 96 includes a plurality of radial protrusions 236 protruding radially inwardly, thereby creating a plurality of dosage grooves 240 therebetween. Upon setting the dosage, the dosage key 228 aligns with one of the dosage grooves 240, and the dosage groove 240 guides the distal movement of the knob 96 relative to the upper body 32 during the injection. In the preferred embodiment, the bearing surface 216 of the dosing stem 88 bottoms out on the proximal end of the sleeve 80. The interaction between the end of the bearing surface 216 and the proximal end of the sleeve 80 provides a physical stop at the end of an injection.

The knob 96 also includes a discontinuous circumferential locking groove 244 radially recessed from an internal surface of the knob 96. A pair of passageways 248 disposed between portions of the locking groove 244 make the locking groove 244 discontinuous. The alignment of the locking protrusions 232 with the passageways 248 permits the proximally displacement of the knob 96 for setting the dose, as described previously. Subsequent to rotation of the knob 96 (and dosing stem 88), the locking protrusions 232 no longer align with the passageways 248. Thus, at the end of the injection stroke, the locking groove 244 engages the locking protrusion 232 of the upper body 32, thereby preventing further displacement of the knob 96 relative to the upper body 32. The interaction between the locking protrusion 232 and the locking groove 244 preferably provides an audible snap so that the user can confirm that the dosing stem 88.has moved forward sufficiently to deliver the desired dosage. Thus, according to one embodiment, the injection device 20 can only be used for one injection. Limiting the injector 20 to a single use can be important in situations where the reconstituted medicament 120 has a limited shelf life. The currently preferred embodiment, therefore, is a disposable device that is discarded after an injection is completed.

Alternative designs are within the scope of this invention, including a reusable device or one that provides multiple dosage settings. The illustrated example includes the ability to deliver a single dosage and is intended to be a single-use device.

Additionally, although reconstitution of a lyophilized medicament has been described above, a pen injector designed according to this invention provides an automated combination of at least two substances for a variety of purposes. Other medicaments, such as those stored in powder form, can be reconstituted. Alternatively, different substances such as multiple vaccines, which must be stored in isolation but can be injected simultaneously, can be combined using the automated combination feature of this invention. Those skilled in the art will realize that an injector designed according to this invention is advantageous for use in a variety of circumstances.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

The invention claimed is:

1. An injection device for automatically combining two substances, comprising:
   a body;
   a cartridge displaceably disposed within the body and having a first chamber for containing a first substance, a second chamber for containing a second substance, a first stopper displaceably disposed within the cartridge and separating the first and second chambers, and a second stopper displaceably disposed within the cartridge and defining an end of the second chamber;
   a needle hub displaceably disposed within the body, the needle hub having threads thereon for connecting a pen needle to the injection device;
   a plunger displaceably disposed within the body;
   a biasing member;
   a sleeve, biased by the biasing member and communicating the bias to the plunger; and
   an activation button radially displaceable with respect to the body to selectively release the sleeve to drive the plunger and automatically mix the first and second substances;
   wherein the activation button comprises:
      a user interface surface; and
      a J-shaped cantilevered arm extending from the user interface surface, the J-shaped cantilevered arm having an opening; and
   wherein the activation button is radially displaceable from a pre-activated position, in which the J-shaped arm retains the sleeve against the bias of the biasing member, to a depressed position to release the sleeve.

2. The injection device according to claim 1, wherein the plunger and at least one of the stoppers displace the needle hub relative to the body to expose the threads for connecting a pen needle thereto.

3. The injection device according to claim 1,
   wherein the plunger and at least one of the stoppers displace the needle hub relative to the body to expose the threads prior to the mixing of the first and second substances.

4. The injection device according to claim 1, further comprising:
   a knob disposed at an end of the body; and
   a dosing stem fixedly connected to the knob for setting a dosage of the combined first and second substances.

5. The injection device according to claim 4, wherein:
   the dosing stem comprises a key extending radially therefrom; and
   the plunger comprises an axial slot;

wherein prior to displacement of the activation button to the depressed position, the axial slot engages the key, preventing rotation of the dosing stem; and wherein subsequent to displacement of the activation button to the depressed position and the displacement of the plunger, the axial slot no longer engages the key, permitting rotation and dose setting of the dosing stem.

6. The injection device according to claim 1, wherein the opening of the J-shaped cantilevered arm is oriented distally.

7. An injection device for automatically combining two substances, comprising:
a body;
a cartridge displaceably disposed within the body and having a first chamber for containing a first substance, a second chamber for containing a second substance, a first stopper displaceably disposed within the cartridge and separating the first and second chambers, and a second stopper displaceably disposed within the cartridge and defining an end of the second chamber;
a needle hub displaceably disposed within the body, the needle hub having threads thereon for connecting a pen needle to the injection device;
a plunger displaceably disposed within the body;
a biasing member;
a sleeve, biased by the biasing member and communicating the bias to the plunger; and
an activation button radially displaceable with respect to the body to selectively release the sleeve to drive the plunger and automatically mix the first and second substances;
wherein the activation button comprises:
a user interface surface; and
a J-shaped cantilevered arm extending from the user interface surface, the J-shaped cantilevered arm having an opening;
wherein the activation button is radially displaceable from a pre-activated position to a depressed position;
wherein the sleeve comprises a central portion and a radial arm extending radially from the central portion;
wherein in the pre-activated position, the J-shaped cantilevered arm retains the radial arm against the bias of the biasing member; and
wherein upon radial displacement of the activation button to the depressed position, the opening of the J-shaped cantilevered arm aligns with the radial arm, permitting displacement of the sleeve.

8. The injection device according to claim 7, wherein the sleeve further comprises a circumferential flange for receiving an end of the biasing member, wherein the radial arm extends from the flange.

9. The injection device according to claim 8, wherein a surface of the flange is substantially planar with a surface of the radial arm.

10. An injection device for automatically combining two substances, comprising:
a body;
a cartridge displaceably disposed within the body and having a first chamber for containing a first substance, a second chamber for containing a second substance, a first stopper displaceably disposed within the cartridge and separating the first and second chambers, and a second stopper displaceably disposed within the cartridge and defining an end of the second chamber;
a needle hub displaceably disposed within the body, the needle hub having threads thereon;
a plunger displaceably disposed within the body;
a biasing member;
a sleeve, biased by the biasing member and communicating the bias to the plunger; and
an activation button radially displaceable with respect to the body to selectively release the sleeve to drive the plunger and displace the needle hub to expose the threads for connection with a pen needle, and automatically mix the first and second substances;
wherein the activation button comprises:
a user interface surface; and
a J-shaped cantilevered arm extending from the user interface surface, the J-shaped cantilevered arm having an opening; and
wherein the activation button is displaceable from a pre-activated position, in which the J-shaped arm retains the sleeve against the bias of the biasing member, to a depressed position.

11. The injection device according to claim 10, wherein the plunger and at least one of the stoppers displace the needle hub relative to the body to expose the threads prior to the mixing of the first and second substances.

12. The injection device according to claim 10, wherein the sleeve comprises a central portion and a radial arm extending radially from the central portion;
wherein in the pre-activated position, the J-shaped cantilevered arm retains the radial arm against the bias of the biasing member; and
wherein upon displacement of the activation button to the depressed position, the opening of the J-shaped cantilevered arm aligns with the radial arm, permitting displacement of the sleeve.

13. The injection device according to claim 12, wherein the sleeve further comprises a circumferential flange for receiving an end of the biasing member, wherein the radial arm extends from the flange.

14. The injection device according to claim 13, wherein a surface of the flange is substantially planar with a surface of the radial arm.

15. The injection device according to claim 10, further comprising:
a knob disposed an end of the body; and
a dosing stem fixedly connected to the knob for setting a dosage of the combined first and second substances.

16. The injection device according to claim 15, wherein:
the dosing stem comprises a key extending radially therefrom; and
the plunger comprises an axial slot;
wherein prior to prior to displacement of the activation button to the depressed position, the axial slot engages the key, preventing rotation of the dosing stem; and
wherein subsequent to displacement of the activation button to the depressed position and the displacement of the plunger, the axial slot no longer engages the key, permitting rotation and dose setting of the dosing stem.

17. The injection device according to claim 10, wherein the opening of the J-shaped cantilevered arm is oriented distally.

18. A method of manufacturing an injection device, comprising:
inserting a cartridge into a body to be displaceable relative to the body, said cartridge having a first chamber for containing a first substance, a second chamber for containing a second substance, a first stopper displaceably disposed within the cartridge and separating the first and second chambers, and a second stopper displaceably disposed within the cartridge and defining an end of the second chamber;

assembling a needle hub to the cartridge body, the needle hub having threads thereon for connecting a pen needle to the injection device;

inserting a plunger into the body to substantially axially align the plunger and the cartridge;

inserting a sleeve onto an end of the plunger;

assembling a radially displaceable activation button with the body to selectively restrain the sleeve from distal displacement, by positioning a J-shaped cantilevered arm of the activation button to restrain the sleeve in a pre-activation position of the activation button, the activation button having a user interface surface, and the J-shaped cantilevered arm having an opening; and assembling a biasing member in the injection device to bias the sleeve, which communicates the bias to the plunger.

19. The method according to claim 18, further comprising assembling a dosing stem to engage the plunger to prevent rotation of the dosing stem relative to the plunger prior to displacement of the activation button.

\* \* \* \* \*